(12) United States Patent
Zilberman et al.

(10) Patent No.: US 6,572,531 B2
(45) Date of Patent: Jun. 3, 2003

(54) IMPLANTABLE MIDDLE EAR IMPLANT

(75) Inventors: Yitzhak Zilberman, Santa Clarita, CA (US); Joseph H. Schulman, Santa Clarita, CA (US)

(73) Assignee: Alfred E. Mann Foundation for Scientific Reseach, Valencia, CA (US)

(*) Notice: Subject to any disclaimer, the term of this patent is extended or adjusted under 35 U.S.C. 154(b) by 0 days.

(21) Appl. No.: 09/882,562

(22) Filed: Jun. 15, 2001

(65) Prior Publication Data

US 2001/0053872 A1 Dec. 20, 2001

Related U.S. Application Data

(60) Provisional application No. 60/212,882, filed on Jun. 16, 2000.

(51) Int. Cl.[7] .............................................. H04R 25/00
(52) U.S. Cl. .............................. 600/25; 607/55; 607/56; 607/57; 381/312
(58) Field of Search ........................... 600/25, 28, 559; 607/55–57; 381/312, 330

(56) References Cited

U.S. PATENT DOCUMENTS

| | | | | |
|---|---|---|---|---|
| 5,411,467 | A | * | 5/1995 | Hortmann et al. ............. 600/25 |
| 5,498,226 | A | * | 3/1996 | Lenkauskas ................... 600/25 |
| 5,772,575 | A | * | 6/1998 | Lesinski et al. ............... 600/25 |
| 5,906,635 | A | | 5/1999 | Maniglia |
| 5,913,815 | A | | 6/1999 | Ball et al. |
| 6,216,040 | B1 | | 4/2001 | Harrison |
| 6,259,951 | B1 | | 7/2001 | Kuzma et al. |
| 6,272,382 | B1 | | 8/2001 | Faltys et al. |
| 6,275,596 | B1 | * | 8/2001 | Fretz et al. .................. 381/321 |
| 6,308,101 | B1 | | 10/2001 | Faltys et al. |

* cited by examiner

Primary Examiner—Gregory Huson
Assistant Examiner—Amanda R. Flynn
(74) Attorney, Agent, or Firm—Lee J. Mandell

(57) ABSTRACT

A hearing aid comprised of conventional cochlear implant electronics implanted in the middle ear and coupled to an actuator configured to mechanically vibrate the middle ear ossicles. The implant electronics, typically used for driving an electrode array implanted in the cochlea, is used instead to supply electric drive signals to the actuator for mechanically vibrating the ossicles.

18 Claims, 2 Drawing Sheets

IMPLANTABLE MIDDLE EAR IMPLANT

RELATED APPLICATIONS

This application claims the benefit of U.S. Provisional Application No. 60/212,882 filed Jun. 16, 2000.

FIELD OF THE INVENTION

This invention relates generally to systems and methods for enhancing hearing in patients suffering from sensorineural hearing loss.

BACKGROUND OF THE INVENTION

Hearing loss is frequently categorized as being either "conductive hearing loss" or "sensorineural hearing loss". Conductive hearing loss typically refers to middle ear impairment and generally results from damage to the tympanic membrane and/or middle ear ossicles. Sensorineural hearing loss is frequently attributable to a reduction in function of hair cells within the cochlea. When sufficiently severe, sensorineural hearing loss can be mitigated by implanting electrodes in the cochlea to electrically stimulate the auditory nerve. When less severe, hearing loss can be mitigated by enhanced activation of the middle ear mechanism. For example, the prior art describes various electrically driven actuator devices for physically contacting and mechanically vibrating the middle ear ossicles.

Great strides have been made in the development of cochlear implant systems for restoring hearing in people suffering from severe sensorineural hearing loss. Such systems are typically comprised of an implant housing containing implant electronics for driving an array of electrodes which are surgically inserted into the cochlea. The implant electronics are typically driven by sound processing electronic circuitry which is generally, but not necessarily, contained in a housing worn externally by the patient. A microphone carried by the patient supplies electric signals to the input of the sound processing circuitry. Typical sound processing circuitry and implant electronics provide for multiple frequency channels.

SUMMARY OF THE INVENTION

The present invention is based on the recognition that existing cochlear implant technology, and particularly devices presently available for implanting in the cochlea to stimulate the auditory nerve, can alternatively be advantageously used in the middle ear to activate the ossicles.

Accordingly, the present invention is directed to a middle ear system comprised of cochlear implant electronics implanted in the middle ear and coupled to an actuator configured to mechanically vibrate the ossicles. A middle ear implant system in accordance with the invention is useful for amplifying sound for patients having reduced, but sufficient, cochlear function.

In accordance with the present invention, implant electronics typically used for driving an electrode array implanted in the cochlea, is used instead to supply electric drive signals to an actuator capable of physically contacting and mechanically vibrating the ossicles. In the case of multichannel implant electronics, it is generally sufficient to map the output drive signal for a single channel to the entire frequency spectrum for driving the actuator.

By combining available technology and devices presently used to electrically stimulate the auditory nerve with existing middle ear actuators, an improved middle ear implant system is provided.

Because middle ear systems in accordance with the invention take advantage of electronic and mechanical design developments from a related but distinct application area, i.e., cochlear implant technology, they can be rapidly and cost effectively provided in accordance with the invention.

DETAILED DESCRIPTION OF THE PREFERRED EMBODIMENTS

Figure 1:
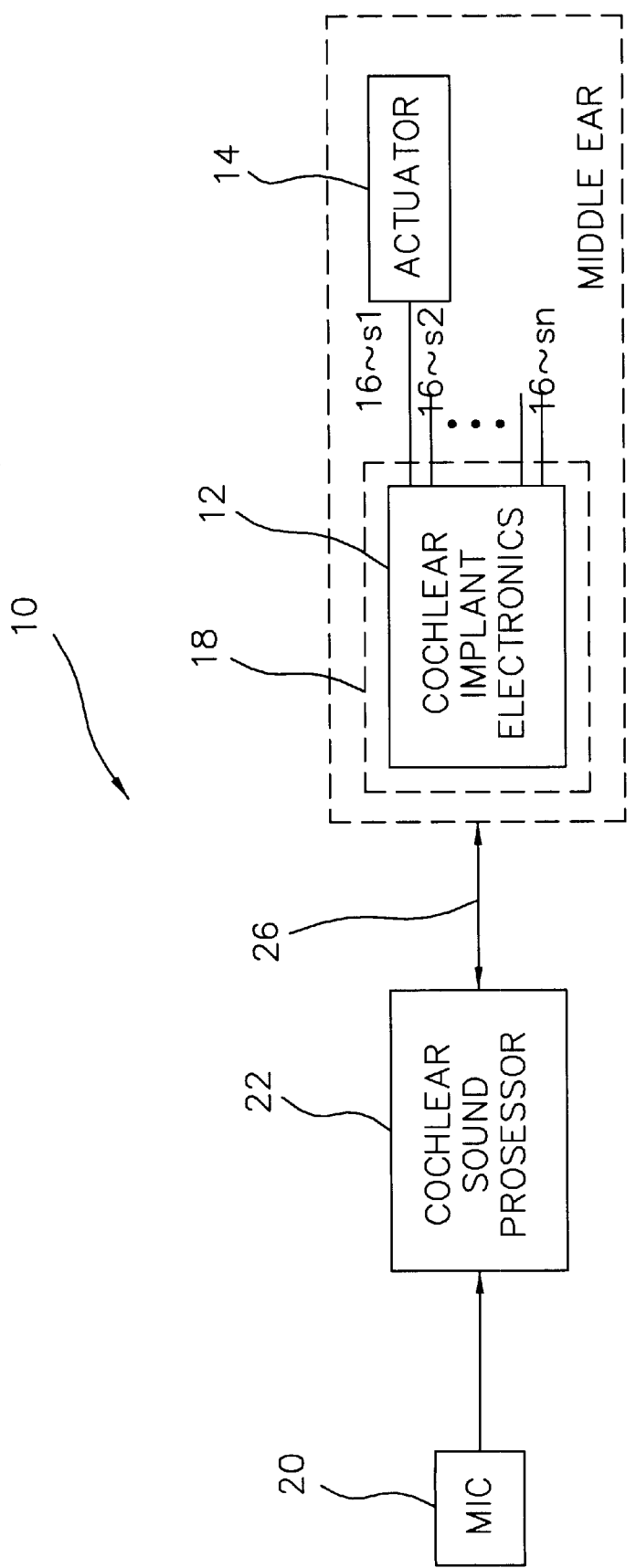
FIG. 1 is a block diagram of a system in accordance with the invention using cochlear implant electronics implanted in the middle ear for driving an actuator to vibrate a patient's ossicles.

Attention is now directed to FIG. 1 which depicts a middle ear implant system 10 in accordance with the present invention. The system 10 employs a digital electronics device 12 for driving an actuator 14 configured to mechanically vibrate the middle ear ossicles. In accordance with the invention, the electronics device 12 and actuator 14 are implanted in a patient's middle ear. An electronics device 12 in accordance with the invention can be substantially identical to electronics devices used in known cochlear implant systems for driving an electrode array (not shown) normally implanted in a patient's cochlea. Suitable cochlear implant electronics devices are commercially available and are discussed in the literature. They are typically provided with multiple output terminals $16_1, 16_2, \ldots 16_n$ for respectively handling different frequency channels. Thus, each of the output terminals 16 would, in a typical cochlear implant application, be connected to a particular group of electrodes implanted in the cochlea. The implant electronics device 12 is typically contained within a hermetically sealed housing 18. In accordance with the present invention, the cochlear implant housing 18 and electronics device 12 are implanted in a patient's middle ear with one or more of the outputs 16, mapped to the entire frequency spectrum, and connected to the actuator 14, also implanted in the patient's middle ear.

A preferred system in accordance with the invention also utilizes a microphone 20 and a conventional cochlear sound processor 22. These devices 12, 20 and 22 are preferably of conventional design, e.g., see the Clarion® digital sound processor and implant electronics. The microphone 20 and sound processor 22 are typically worn externally by the patient. That is, the patient could wear the sound processor 22 behind the ear or carried on a belt. However, it is also contemplated that the microphone 20 and sound processor 22 can be implanted, e.g., in the middle ear or near the outer ear. The sound processor 22 preferably incorporates an analog-to-digital converter which accepts an analog signal from the microphone and converts it to digital form for processing in sound processor 22. Alternatively, the analog-to-digital converter can comprise a distinct device connected between the microphone 20 and sound processor 22. Depending upon the particular implantation site, the sound processor 22 communicates with the implant electronics device 12 via a communication channel 26. This channel 26 could comprise a wire but preferably comprises a wireless channel, e.g., a radio frequency channel. If radio frequency communication is used, the sound processor 22 would include communication components including a signal modulator and transmitter. The implant electronics device 12 would likewise include a receiver and demodulator.

Cochlear implant systems normally have the ability to program the parameters of the cochlear implant electronics by transmitting commands via communication channel 26 to the implant electronics device 12. The implant electronics device 12 also preferably has the ability to transmit information, e.g., status, back to the sound processor 22.

Figure 2:
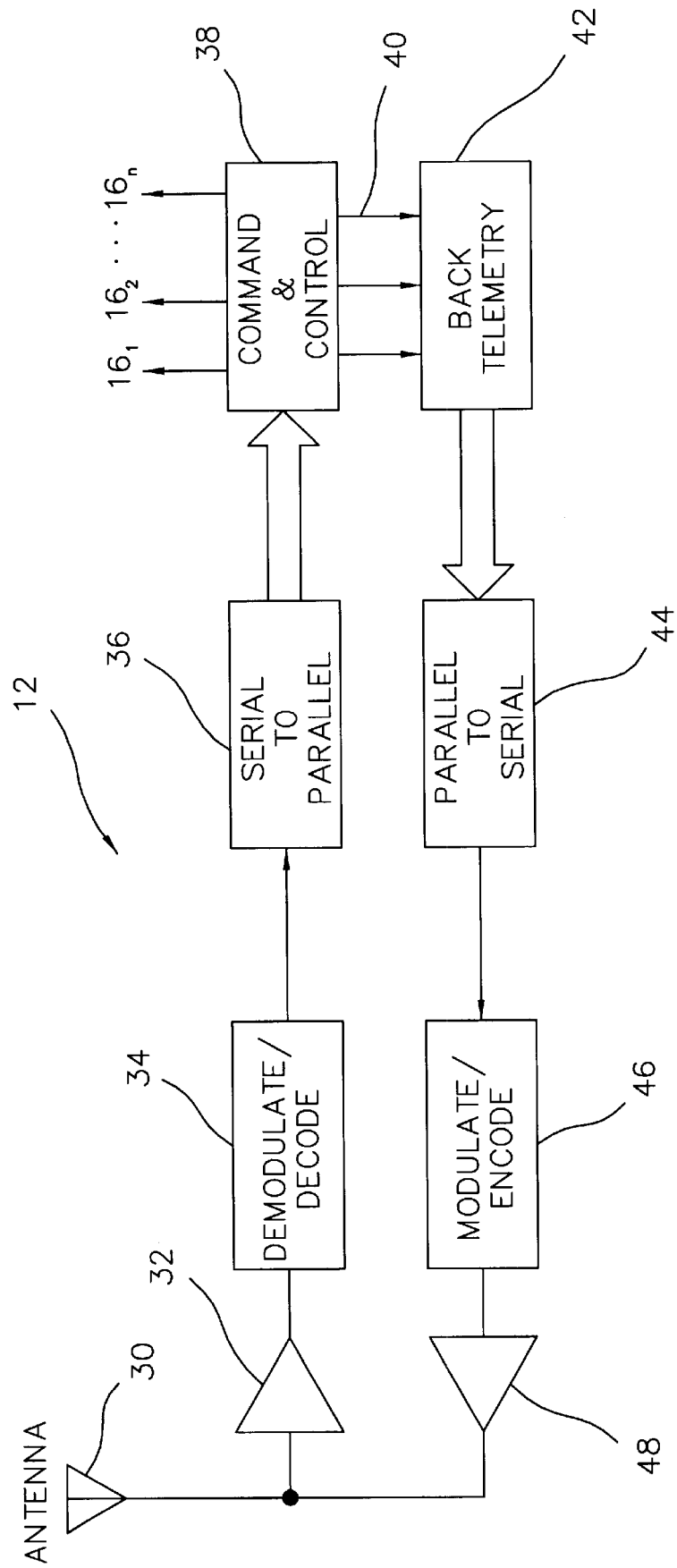
FIG. 2 is a block diagram of a portion of the exemplary cochlear implant electronics device of FIG. 1.

FIG. 2 comprises a block diagram representative of the conventional cochlear implant electronics device 12. It includes an antenna 30 coupled via an amplifier 32 to a demodulate/decode circuit 34. The demodulated and decoded signals out of circuit 34 are then typically converted from serial to parallel form in converter 36 and applied to a command and control circuit 38. The circuit 38 processes the applied signals to produce output signals at output terminal $16_1$–$16_n$, (FIG. 1) for driving actuator 14. Additionally, circuitry 38 supplies signals via outputs 40 to telemetry circuit 42 which supplies a parallel digital signal to parallel to serial converter 44. The output of converter 44 is supplied to a modulate/encode circuit 46 which is then delivered via amplifier 48 to the antenna 30 for transmission back to the sound processor 22.

The actuator 14 can comprise a conventional device implanted in the middle ear for mechanically vibrating the middle ear bones (ossicles) preferably by direct physical contact. For example, see the apparatus described in U.S. Pat. No. 5,913,815 issued Jun. 22, 1999.

It is intended that all of the implanted electronics be battery operated. Thus, in preferred embodiments of the invention, a battery, preferably a rechargeable lithium ion battery, is included in the implanted electronics. A charging circuit is preferably also included in the implanted electronics package for responding to an alternating magnetic field provided by an external power source for producing a charging current for the battery.

From the foregoing, it should now be appreciated that an improved middle ear hearing aid system has been disclosed comprised of conventional cochlear implant electronics implanted in the middle ear to drive an actuator configured to vibrate the middle ear ossicles.

What is claimed is:

1. A system for enhancing a patient's hearing capability by mechanically stimulating ossicles in the middle ear of the patient using a cochlear implant device otherwise capable of electrical stimulation of neuro pathways in the cochlea of the patient, said system comprising:

an actuator implantable in the patient's middle ear energizable to mechanically vibrate the patient's middle ear ossicles;

a cochlear implant device having a plurality of output terminals configurable to drive a cochlear electrode array for electrical stimulation of neuro pathways in the cochlea of the patient wherein said cochlear implant device is instead configured for producing an output drive signal on at least one of said output terminals for energizing said actuator;

a microphone for producing electric signals representative of sound energy incident thereon; and a sound processor responsive to said electric signals produced by said microphone for producing digital signals for application to said cochlear implant device.

2. The system of claim 1 wherein said sound processor is externally carried by said patient.

3. The system of claim 1 wherein said sound processor is internally carried by said patient.

4. The system of claim 1 wherein none of said output terminals are coupled to a cochlear electrode array.

5. The system of claim 1 wherein said actuator is configured to mechanically vibrate the ossicles via direct physical contact.

6. The system of claim 1 wherein said cochlear implant device is configurable to provide different frequency-related signals to each of said output terminals of said cochlear implant device and said cochlear implant device is configured to provide said output drive signal mapped to the entire frequency spectrum to said actuator.

7. The system of claim 6 wherein none of said output terminals are coupled to a cochlear electrode array.

8. A method for enhancing a patient's hearing by mechanically stimulating ossicles in the middle ear of the patient using a multichannel electronic device otherwise capable of electrical stimulation of neuro pathways in the cochlea of the patient, said method comprising:

implanting in the patient's middle ear an actuator for mechanically vibrating the patient's middle ear ossicles;

implanting in the patient's middle ear a multichannel electronic device suitable for driving a cochlear electrode array but instead configured for driving said mechanical actuator; and connecting at least one channel output of said electronic device to said actuator.

9. The method of claim 8 further including:

providing a microphone for producing electric signals representative of sound energy incident thereon; and providing a sound processor responsive to said microphone produced electric signals for controlling said electronic device.

10. The method of claim 8 wherein none of said output terminals are coupled to a cochlear electrode array.

11. The method of claim 8 wherein said implanting step further comprises implanting said actuator in direct physical contact with the ossicles.

12. The method of claim 8 wherein said multichannel electronic device is a cochlear implant device configurable to provide different frequency-related signals to each of said output terminals of said cochlear implant device, further comprising the step of configuring said cochlear implant device to provide said output drive signal mapped to the entire frequency spectrum to said actuator.

13. The method of claim 12 further comprising the step of ensuring that none of said output terminals are coupled to a cochlear electrode array.

14. A system for enhancing a patient's hearing by mechanically stimulating ossicles in the middle ear of the patient using a cochlear implant device otherwise capable of electrical stimulation of neuro pathways in the cochlea of the patient, said system comprising:

an actuator implanted in the patient's middle ear energizable to mechanically vibrate the patient's middle ear ossicles; and a multiple output channel electronic device suitable for driving an implanted cochlear electrode array to electrically stimulate neuro pathways in the cochlea of the patient but instead configured to provide an output signal mapped to the entire spectrum for driving said mechanical actuator;

said electronic device being implanted in the patient's middle ear; and means connecting at least one of said electronic device output channels to said actuator for energizing said actuator to mechanically vibrate the patient's ossicles.

15. The system of claim 14 wherein none of said output terminals are coupled to a cochlear electrode array.

16. The system of claim 14 wherein said actuator is configured to mechanically vibrate the ossicles via direct physical contact.

17. The system of claim 14 wherein said cochlear implant device is configurable to provide different frequency-related signals to each of said output terminals of said cochlear implant device and said cochlear implant device is config ured to provide said output drive signal mapped to the entire frequency spectrum to said actuator.

18. The system of claim 17 wherein none of said output terminals are coupled to a cochlear electrode array.

* * * * *